United States Patent [19]

Cimarusti

[11] 4,052,422

[45] Oct. 4, 1977

[54] 4,5-SECOPREGNANE DERIVATIVES

[75] Inventor: Christopher M. Cimarusti, Hamilton, N.J.

[73] Assignee: E. R. Squibb & Sons, Inc., Princeton, N.J.

[21] Appl. No.: 522,178

[22] Filed: Nov. 8, 1974

[51] Int. Cl.$^2$ .................. C07C 49/26; C07C 69/18; C07C 69/30; C07C 69/78
[52] U.S. Cl. ........................ 260/408; 260/410; 260/456 R; 260/586 E; 424/308; 424/311; 424/312; 424/331; 560/107; 560/256; 560/72
[58] Field of Search ............ 260/410, 488 B, 586 E, 260/408, 476 C

[56] References Cited

U.S. PATENT DOCUMENTS

| | | |
|---|---|---|
| 3,048,531 | 8/1962 | Fried .......................... 260/239.55 |
| 3,102,145 | 8/1963 | Nominé et al. ............... 260/586 E |
| 3,499,912 | 3/1970 | Uskokovic et al. ........... 260/343.2 |
| 3,766,256 | 10/1973 | Uskokovic et al. .......... 260/586 E |
| 3,796,728 | 3/1974 | Tanabe ......................... 260/345.9 |
| 3,835,160 | 9/1974 | Tanabe ......................... 260/340.9 |

FOREIGN PATENT DOCUMENTS

| | | | |
|---|---|---|---|
| 1,257,111 | 12/1971 | United Kingdom ............ 260/586 E |
| 1,211,697 | 11/1970 | United Kingdom ............ 260/586 E |

OTHER PUBLICATIONS

Chem. Abstracts, 70:88108v (1969).
Chem. Abstracts, 68:69183h (1968).

*Primary Examiner*—Vivian Garner
*Attorney, Agent, or Firm*—Lawrence S. Levinson; Merle J. Smith; Donald J. Barrack

[57] ABSTRACT

Novel 4,5-seco-steroids having anti-inflammatory activity are disclosed herein.

13 Claims, No Drawings

4,5-SECOPREGNANE DERIVATIVES

SUMMARY OF THE INVENTION

Compounds having the formula

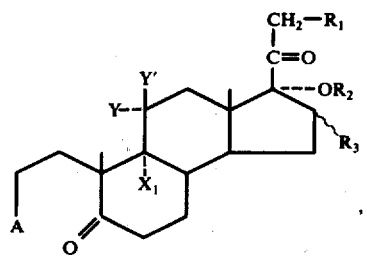

I are useful as anti-inflammatory agents. In formula I, and throughout the specification, the symbols have the following meaning:

A can be —C≡CH, —CH=CH$_2$, —CH$_2$CH$_3$, or

$X_1$ can be hydrogen, chlorine, bromine or fluorine;
$R_1$ can be hydrogen, hydroxyl,

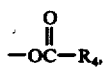

chlorine, bromine, fluorine or iodine;
$R_2$ can be hydrogen or

$R_3$ can be hydrogen, α-methyl, β-methyl, or methylene;
$R_4$ can be lower alkyl or aryl; and
Y can be hydrogen and Y' can be hydroxyl or together Y and Y' can be =O.

The expression "lower alkyl" refers to both straight and branched chain alkyl groups having 1 to 7 carbon atoms; e.g., methyl, ethyl, propyl, isopropyl, t-butyl, heptyl, etc. Alkyl groups having 1 to 3 carbon atoms are preferred.

The term "aryl" refers to phenyl or phenyl substituted with halogen, alkyl or alkoxy. Phenyl is the preferred aryl group.

DETAILED DESCRIPTION OF THE INVENTION

The compounds of formula I are physiologically active substances that possess anti-inflammatory activity, as shown by the reversed passive Arthus skin reaction and the mouse active Arthus reaction, and can be used in various mammalian species such as domestic animals, e.g., dogs and cats. They can be used to decrease joint swelling, tenderness, pain and stiffness in conditions such as rheumatoid arthritis. Surprisingly, in the 4,5-seco-steroids of this invention hormonal side effects are greatly reduced or eliminated in comparison to the 3-keto-Δ$^4$-steroid starting materials (see formula II below).

A compound of formula I can be compounded according to acceptable pharmaceutical practice in oral dosage forms such as tablets, capsules, elixirs or powders, for administration in an amount of about 100 mg/kg/day to 2 gm/kg/day, preferably 100 mg/kg/day to 1 gm/kg/day, in a single dose or in divided doses.

Compounds of formula I, wherein $R_1$ is

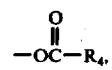

$R_2$ is

and $X_1$ is hydrogen or fluorine, can be prepared using as starting materials, compounds have the structure

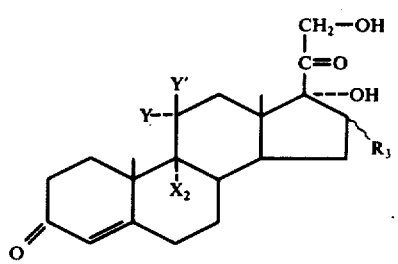

II

In formula II, and throughout the specification, $X_2$ can be hydrogen or fluorine.

Initially, the 17,21-dihydroxy-20-keto moiety of the steroid of formula II must be protected. Many blocking methods will be apparent to those skilled in the art. It is preferred, however, to react a steroid of formula II with a compound having the structure

III ($R_5$ is alkyl of 1 to 4 carbon atoms) to yield a steroid having the structure

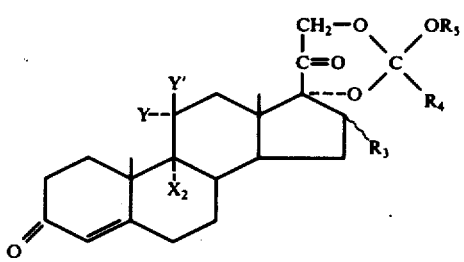

IV

The reaction can be run in a polar organic solvent, e.g., dimethylformamide, dimethylsulfoxide, etc., in the presence of an organic acid, e.g., p-toluenesulfonic acid. Reaction conditions can be from about 20° to 140° C, for about 2 hours to 24 hours.

Another suitable protecting group which can be used is the bis-(methylenedioxy) group (known as "BMD"); cf. Steroid Reactions, C. Djerassi editor, page 956 and references cited therein (1963).

Reaction of a steroid of formula IV with hydrogen peroxide in the presence of alkali, e.g., potassium hydroxide, sodium hydroxide, etc. yields a 4,5-epoxy steroid having the structure

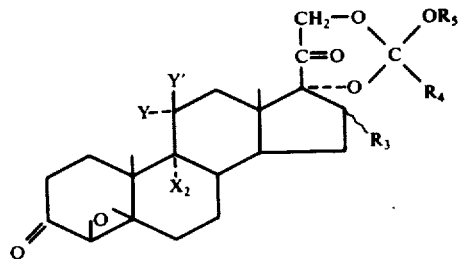

V

The reaction is run in a polar organic solvent, preferably a lower alkanol such as methanol, at a temperature of about 0° to 40° C for 2 hours to 168 hours, preferably at room temperature for 72 hours to 120 hours.

Hydrolysis of a steroid of formula V with a suitable acid yields a steroid having the structure

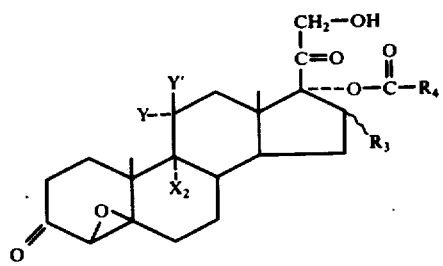

VI

The hydrolysis can be performed in the manner described by R. Vitali and R. Gardi (Il Farmaco, Ed. Sc. 27, 818 (1972)) utilizing a methanol solution of the steroid of formula V and an acetic acid-sodium acetate buffer.

Acylation of a steroid of formula VI with a suitable acylating agent, e.g., an acid halide of the formula

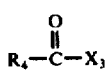

(wherein $X_3$ is halogen) or an acid anhydride of the formula $(R_4CO)_2O$, yields a steroid having the structure

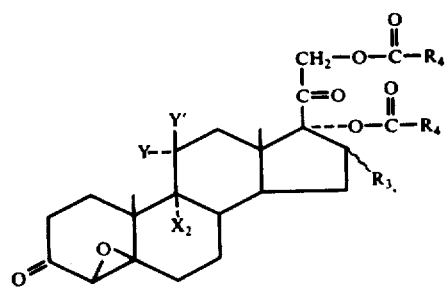

VII

The 4,5-epoxy steroid of formula VII is reacted with p-toluenesulfonylhydrazide to yield a 4,5-seco-steroid of formula I wherein $R_1$ is

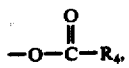

$X_1$ is hydrogen or fluorine and A is —C≡CH, i.e., compounds having the structure

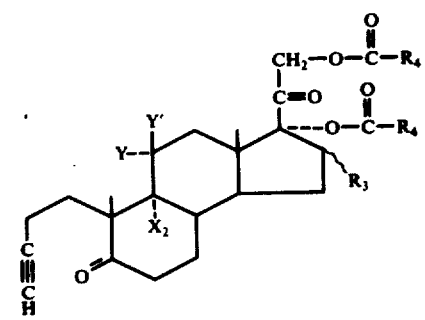

VIII

The reaction is run in an organic solvent, or a mixture of organic solvents, such as halogenated hydrocarbons at a temperature of from 0° to 40° C for 2 hours to 24 hours, preferably at from 0° C to room temperature for 4 hours to 16 hours.

Compounds of formula I wherein $R_1$ is

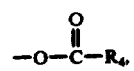

$R_2$ is

$X_1$ is hydrogen or fluorine, and A is

i.e., compounds having the structure

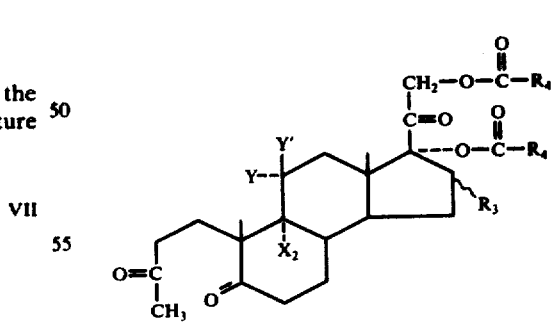

IX can be prepared by hydrating a compound of formula VIII in the presence of mercuric sulfate. The reaction is carried out in an acid medium, e.g. a mixture of formic or acetic acid and a lower alkanol such as methanol, at a temperature of from about 0° to 80° C for about 30 minutes to 24 hours, preferably at 50° to 70° C for 30 minutes to 2 hours.

Reduction of a compound of formula VIII yields a compound of formula I wherein $R_1$ is $R_2$ is

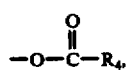

$X_1$ is hydrogen or fluorine, and A is —$CH_2CH_3$, i.e. a compound having the structure

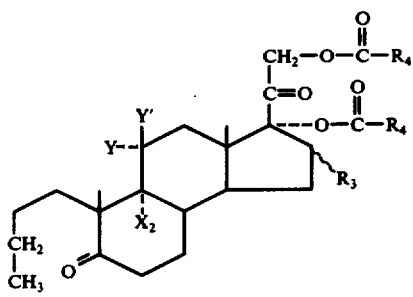

Reduction can be carried out at atmospheric pressure using gaseous hydrogen with a catalyst such as palladium or platinum oxide.

Partial reduction of a compound of formula VIII yields a compound of formula I wherein $R_1$ is

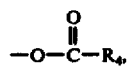

$R_2$ is

$X_1$ is hydrogen or fluorine, and A is —CH=$CH_2$, i.e., a compound having the structure

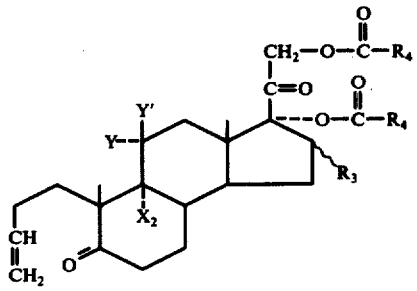

The reduction can be carried out at atmospheric pressure using a small amount (i.e., about 0.1–5.0% by weight) of a poisoned catalyst, e.g., palladium poisoned with synthetic guinoline.

Compounds of formula I wherein $R_1$ is hydroxyl or $R_2$ is hydrogen can be prepared by saponification of the corresponding 21-alkanoyloxy or 17-alkanoyloxy compound of formula I. The saponification reaction can be carried out using procedures well known in the art.

Compounds of formula I wherein $R_1$ is hydrogen or halogen can be prepared from the corresponding 21-hydroxyl compounds using methods well known in the art. Reaction of a 21-hydroxyl compound of formula I with a lower alkyl (or aryl) sulfonyl chloride (e.g., methanesulfonyl chloride or p-toluenesulfonyl chloride) yields the corresponding 21-sulfonate. The reaction can be carried out in the presence of an organic base such as pyridine, at a temperature of from about 0° to 20° C under anhydrous conditions. Reaction of the 21-sulfonate with an inorganic halide (e.g., sodium iodide, lithium chloride, lithium bromide, potassium fluoride, etc.) yields the corresponding 21-iodo-, 21-chloro-, 21-bromo, and 21-fluoro, compounds of formula I. The reaction is conducted in a polar organic solvent (e.g., dimethylformamide, acetone, etc.) under reflux conditions for about 1 hour to 12 hours, preferably about 2 hours to 4 hours. Reaction of the 21-sulfonate with sodium iodide in glacial acetic acid at a temperature of about 20° to 100° C yields a compound of formula I wherein $R_1$ is hydrogen.

Compounds of formula I wherein $X_1$ is chlorine or bromine can be prepared from the corresponding compound of formula I wherein $X_1$ is hydrogen, Y is hydrogen, Y' is hydroxyl, i.e., a compound having the structure

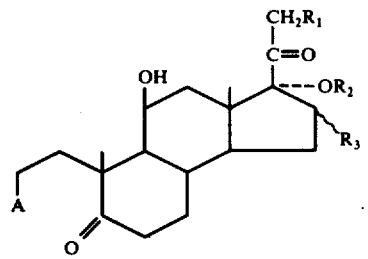

Reaction of a compound of formula XII, when $R_1$ is other than hydroxyl, with a lower alkylsulfonyl chloride in a polar organic solvent, e.g., dimethylformamide, in the presence of an organic base, e.g., pyridine, yields a $\Delta^{9(11)}$-compound having the structure

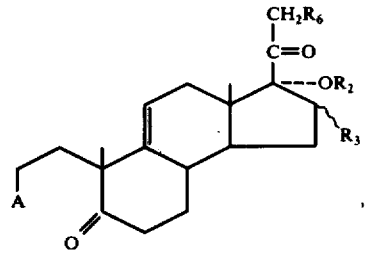

wherein $R_6$ is hydrogen,

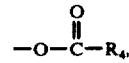

chlorine, bromine, fluorine, or iodine. The reaction can be run at room temperature for about 4 hours to 24 hours, preferably for about 4 hours to 12 hours.

The process for preparing a 9α-chloro- or a 9α-bromo-compound of formula I from an intermediate of formula XIII is known; see, for example, U.S. Pat. No. 2,852,511 to Josef Fried.

Compounds of formula I wherein $R_1$ is hydroxyl and $X_1$ is chlorine or bromine are prepared as described above, except that two additional steps are required. Before reacting the compound of formula XII with lower alkylsulfonyl chloride to obtain a $\Delta^{9(11)}$-compound, the 21-hydroxyl group must be protected (e.g., by reaction of the compound with acetic anhydride). After the 9α-chloro- or 9α-bromo-compound is formed, the protecting group is removed by reaction with a base.

Compounds of formula I wherein $X_1$ is hydrogen or fluorine are preferred, and those wherein $X_1$ is fluorine are particularly preferred.

Compounds of formula I wherein Y is hydrogen and Y' is hydroxyl are preferred.

The following examples are specific embodiments of the above described invention.

EXAMPLE 1

17,21-bis(Acetyloxy)-9-fluoro-11β-hydroxy-4,5-seco-pregn-3-yne-5,20-dione

A. 9-Fluoro-11β,17,21-trihydroxypregn-4-ene-3,20-dione, cyclic 17,21-methyl orthoacetate A mixture of 38 g of 9-fluoro-11β,17,21-trihydroxypregn-4-ene-3,20-dione, 76 ml of dimethylformamide, 76 ml of trimethyl orthoacetate, and 300 mg of p-toluenesulfonic acid is stirred at 125° C for 4 hours, cooled, and 4 ml of pyridine is added. The mixture is poured into water and the crystalline product filtered to give 50.1 g of crude product. Chromatography on a 500 g silica gel column, eluting with dichloromethane, yields 27.3 g of the title compound.

B. 4β,5-Epoxy-9-fluoro-11β,17,21-trihydroxypregnane-3,20-dione, cyclic 17,21-methyl orthoacetate A solution of 12.5 g of 9-fluoro-11β,17,21-trihydroxypregn-4-ene-3,20-dione, cyclic 17,21-methyl orthoacetate in 1.25 liters of methanol is stirred for 4 days with 30 ml of 30% hydrogen peroxide and 20 ml of 4 N sodium hydroxide solution. The solution is diluted with water and filtered to give a solid. This is dissolved in dichloromethane, dried, and evaporated to yield 9.0 g of the title compound.

C. 17,21-bis(Acetyloxy)-4β,5-epoxy-9-fluoro-11β-hydroxypregnane-3,20-dione

A solution of 8 g of 4β,5-epoxy-9-fluoro-11β,17,21-trihydroxypregnane-3,20-dione, cyclic 17,21-methyl orthoacetate in 600 ml of methanol is refluxed for 90 minutes with 100 ml of a buffer solution (90 ml of 0.1 N acetic acid and 10 ml of 0.1 M sodium acetate). The solution is cooled, poured into 2 liters of water, and extracted with dichloromethane to give the crude 17-acetate after solvent removal. This is dissolved in 30 ml of pyridine and 10 ml of acetic anhydride added. After 4 hours the solvent is removed in vacuo and a dichloromethane solution of the residue is washed with 5% hydrochloric acid, water, and dried. Solvent removal yields 8.8 g of crude product which is chromatographed on a 120 g-silica gel column. Elution with dichloromethane yields 4.3 g of the title compound.

D. 17,21-bis(Acetyloxy)-9-fluoro-11β-hydroxy-4,5-secopregn-3-yne-5,20-dione

A solution of 4.6 g of 17,21-bis(acetyloxy)-4β,5-epoxy-9-fluoro-11β-hydroxypregnane-3,20-dione in 300 ml of 1:1 acetic acid-dichloromethane is treated dropwise with a solution of 1.8 g of p-toluenesulfonylhydrazide in 300 ml of the same solvent. After stirring overnight at ambient temperature the mixture is diluted with dichloromethane, washed with water and aqueous sodium bicarbonate, dried, and evaporated to give 4.15 g of crude product. This is chromatographed on a 100 g-silica gel column to give 3.4 g of the title compound.

EXAMPLE 2

17,21-bis(Acetyloxy)-9-fluoro-11β-hydroxy-4,5-secopregnane-5,20-dione

A solution of 3.4 g of 17,21-bis(acetyloxy)-9-fluoro-11β-hydroxy-4,5-secopregn-3-yne-5,20-dione in 340 ml of ethyl acetate is stirred in an atmosphere of hydrogen with 340 mg of 5% Pd/C. After 155 minutes hydrogen uptake (400 ml) ceases and the slurry is filtered and evaporated in vacuo. The crude product is chromatographed on a 60 g-silica gel column to give 2.01 g of the title compound.

EXAMPLE 3

17,21-bis(Acetyloxy)-9-fluoro-11β-hydroxy-4,5-secopregnane-3,5,20-trione

A solution of 670 mg of 17,21-bis(acetyloxy)-9-fluoro-11β-hydroxy-4,5-secopregn-3-yne-5,20-dione in a mixture of 8.3 ml of 85% formic acid and 8.3 ml of 80% aqueous methanol is heated at 60° C for 30 minutes with a solution prepared from 50 mg of mercuric oxide, 0.08 ml of sulfuric acid and 1.9 ml of water. The solution is cooled, diluted with water and extracted with chloroform. The chloroform solution is washed with water, dilute sodium carbonate solution and dried. The solvent is evaporated in vacuo to yield the title compound.

EXAMPLE 4

17,21-bis(Acetyloxy)-9-fluoro-11β-hydroxy-4,5-secopregn-3-ene-5,20-dione

A solution of 3.0 g of 17,21-bis(acetyloxy)-9-fluoro-11β-hydroxy-4,5-secopregn-3-yne-5,20-dione in 300 ml of ethyl acetate containing 50 mg of synthetic guinoline and 30 mg of 5% Pd/BaSO₄ is stirred at room temperature under 1.0 atmosphere of hydrogen for 15 hours to yield the title compound.

EXAMPLE 5

9-Fluoro-11β,17,21-trihydroxy-4,5-secopregnane-5,20-dione

A solution of 1 g of 17,21-bis(acetyloxy)-9-fluoro-11β-hydroxy-4,5-secopregnane-5,20-dione in 20 ml of methanol and 2 ml of 10% aqueous potassium carbonate is stirred under nitrogen for 1 hour. The solution is acidified with 10% acetic acid and extracted with dichloromethane to give 750 mg of crude product. This is combined with 1.13 g of similar material and chromatographed on a 50 g-silica gel column. Elution with 3:1 dichloromethane-ethyl acetate yields 1.15 g of material which crystallizes from methanol to give 800 mg of the title compound, melting point 216°–218° C, with decomposition.

EXAMPLE 6

21-(Acetyloxy)-9-fluoro-11β,17-dihydroxy-4,5-secopregnane-5,20-dione

A solution of 2.1 g of 9-fluoro-11β,17,21-trihydroxy-4,5-secopregnane-5,20-dione in 21 ml of pyridine and 2 ml of acetic anhydride is stirred for 4 hours at room temperature and the solvents are evaporated in vacuo. The residue is dissolved in chloroform and the resulting solution is washed with dilute sodium bicarbonate, water, dilute hydrochloric acid and dried. Removal of the solvent in vacuo yields the title compound.

EXAMPLE 7

21-Chloro-9-fluoro-11β,17-dihydroxy-4,5-secopregnane-5,20-dione

A. 21-(Mesyloxy)-9-fluoro-11β,17-dihydroxy-4,5-secopregnane-5,20-dione

A solution of 1.4 g of 9-fluoro-11β,17,21-trihydroxy-4,5-secopregnane-5,20-dione in 14 ml of pyridine is stirred at 0° C for 2 hours with 0.3 ml of methanesulfonyl chloride. The resulting solution is poured into cold dilute hydrochloric acid and extracted with chloroform. The chloroform solution is washed with dilute bicarbonate solution, dried and evaporated to give the title compound.

B. 21-Chloro-9-fluoro-11β,17-dihydroxy-4,5-secopregnane-5,20-dione

A solution of 1.48 g of 21-(mesyloxy)-9-fluoro-11β,17-dihydroxy-4,5-secopregnane-5,20-dione in 20 ml of dimethylformamide is refluxed with 2 g of lithium chloride for 1 hour, cooled and poured into ice water. The resulting solid is filtered to give the title compound.

EXAMPLE 8

21-Bromo-9-fluoro-11β,17-dihydroxy-4,5-secopregnane-5,20-dione

A solution of 1.48 g of 21-(mesyloxy)-9-fluoro-11β,17-dihydroxy-4,5-secopregnane-5,20-dione in 20 ml of dimethylformamide is refluxed with 2.4 g of lithium bromide for 1 hour, cooled and poured into ice water. The resulting solid is filtered to give the title compound.

EXAMPLE 9

9-Fluoro-11β,17-dihydroxy-4,5-secopregnane-5,20-dione

A solution of 0.4 g of 21-(mesyloxy)-9-fluoro-11β,17-dihydroxy-4,5-secopregnane-5,20-dione in 20 ml of glacial acetic acid is heated at 100° C with 1.9 g of sodium iodide for 2 hours, cooled and poured into dilute bicarbonate solution. The slurry is extracted with chloroform and the chloroform solution is washed with sodium bisulfite solution, dried and evaporated in vacuo to give the title compound.

EXAMPLE 10

9,21-Difluoro-11β,17-dihydroxy-4,5-seco-pregnane-5,20-dione

A solution of 2.1 g of 21-(mesyloxy)-9-fluoro-11β,17-dihydroxy-4,5-secopregnane-5,20-dione in 30 ml of dimethylsulfoxide is refluxed for 6 hours with 3 g of potassium fluoride, cooled and poured into ice water. The resulting slurry is extracted with chloroform and the solution is washed several times with dilute hydrochloric acid and dried. Evaporation of the solvent in vacuo yields the title compound.

EXAMPLES 11 – 13

Following the procedure of Example 1, but substituting the steroid listed in column I for 9-fluoro-11β,17,21-trihydroxypregn-4-ene-3,20-dione, the compound listed in column II is obtained.

| Example | Column I | Column II |
|---|---|---|
| 11 | 9-fluoro-16α-methyl-11β,17,21-trihydroxypregn-4-ene-3,20-dione | 17,21-bis(acetyloxy)-9-fluoro-11β-hydroxy-16α-methyl-4,5-secopregn-3-yne-5,20-dione |
| 12 | 9-fluoro-16-methylene-11β,17,21-trihydroxypregn-4-ene-3,20-dione | 17,21-bis(acetyloxy)-9-fluoro-11β-hydroxy-16-methylene-4,5-secopregn-3-yne-5,20-dione |
| 13 | 9-fluoro-16β-methyl-11β,17,21-trihydroxypregn-4-ene-3,20-dione | 17,21-bis(acetyloxy)-9-fluoro-11β-hydroxy-16β-methyl-4,5-secopregn-3-yne-5,20-dione |

EXAMPLES 14 – 16

Following the procedure of Example 2, but substituting the compound listed in column I for 17,21-bis-(acetyloxy)-9-fluoro-11β-hydroxy-4,5-secopregn-3-yne-5,20-dione, the compound listed in colunn II is obtained.

| Example | Column I | Column II |
|---|---|---|
| 14 | 17,21-bis(acetyloxy)-9-fluoro-11β-hydroxy-16α-methyl-4,5-secopregn-3-yne-5,20-dione | 17,21-bis(acetyloxy)-9-flouro-11β-hydroxy-16α-methyl-4,5-secopregnane-5,20-dione, melting point 181-183° C, dec. |
| 15 | 17,21-bis(acetyloxy)-9-fluoro-11β-hydroxy-16-methylene-4,5-secopregn-3-yne-5,20-dione | 17,21-bis(acetyloxy)-9-flouro-11β-hydroxy-16-methylene-4,5-secopregnane-5,20-dione- |
| 16 | 17,21-bis(acetyloxy)-9-fluoro-11β-hydroxy-16β-methyl-4,5-secopregn-3-yne-5,20-dione | 17,21-bis(acetyloxy)-9-fluoro-11β-hydroxy-16β-methyl-4,5-secopregnane-5,20-dione |

EXAMPLES 17 – 19

Following the procedure of Example 3, but substituting the compound listed in column I for 17,21-bis-(acetyloxy)-9-fluoro-11β-hydroxy-4,5-secopregn-3-yne-5,20-dione, the compound listed in column II is obtained.

| Example | Column I | Column II |
|---|---|---|
| 17 | 17,21-bis(acetyloxy)-9-fluoro-11β-hydroxy-16α-methyl-4,5-secopregn-3-yne-5,20-dione | 17,21-bis(acetyloxy)-9-fluoro-11β-hydroxy-16α-methyl-4,5-secopregnane-3,5,20-trione |
| 18 | 17,21-bis(acetyloxy)-9-fluoro-11β-hydroxy-16-methylene-4,5-secopregn-3-yne-5,20-dione | 17,21-bis(acetyloxy)-9-fluoro-11β-hydroxy-16-methylene-4,5-secopregnane-3,5,20-trione |
| 19 | 17,21-bis(acetyloxy)-9-fluoro-11β-hydroxy-16β-methyl-4,5-secopregn-3-yne-5,20-dione | 17,21-bis(acetyloxy)-9-fluoro-11β-hydroxy-16β-methyl-4,5-secopregnane-3,5,20-trione |

EXAMPLES 20 – 22

Following the procedure of Example 4, but substituting the compound listed in column I for 17,21-bis-(acetyloxy)-9-fluoro-11β-hydroxy-4,5-secopregn-3-yne-5,20-dione, the compound listed in column II is obtained.

| Example | Column I | Column II |
|---|---|---|
| 20 | 17,21-bis(acetyloxy)-9-fluoro-11β-hydroxy-16α-methyl-4,5-secopregn-3-yne-5,20-dione | 17,21-bis(acetyloxy)-9-flouro-11β-hydroxy-16α-methyl-4,5-secopregn-3-ene-5,20-dione |
| 21 | 17,21-bis(acetyloxy)-9-fluoro-11β-hydroxy-16-methylene-4,5-secopregn-3-yne-5,20-dione | 17,21-bis(acetyloxy)-9-fluoro-11β-hydroxy-16-methylene-4,5-secopregn-3-ene-5,20-dione |
| 22 | 17,21-bis(acetyloxy)-9-fluoro-11β-hydroxy-16β-methyl-4,5-secopregn-3-yne-5,20-dione | 17,21-bis(acetyloxy)-9-flouro-11β-hydroxy-16β-methyl-4,5-secopregn-3-ene-5,20-dione |

EXAMPLES 23 – 24

Following the procedure of Example 6, but substituting the reactant listed in column I for acetic anhydride, the compound listed in column II is obtained.

| Example | Column I | Column II |
|---|---|---|
| 23 | benzoyl chloride | 21-(benzoyloxy)-9-fluoro-11β,17-dihydroxy-4,5-secopregnane-5,20-dione |
| 24 | p-chlorobenzoic anhydride | 21-(p-chlorobenzoyloxy)-9-fluoro-11β,17-dihydroxy-4,5-secopregnane-5,20-dione |

EXAMPLE 25

17,21-bis(Acetyloxy)-9-bromo-11β-hydroxy-4,5-secopregn-3-yne-5,20-dione

A. 17,21-bis(Acetyloxy)-4,5-secopregn-9(11)-ene-3-yne-5,20-dione

A solution of 17,21-bis(acetyloxy)-11β-hydroxy-4,5-secopregn-3-yne-5,20-dione (4 mmole) in 20 ml of dimethyl-formamide and 20 ml of pyridine is stirred at ambient temperature with 10 ml of methanesulfonyl chloride for 2 hours, poured into cold dilute hydrochloric acid, and extracted with chloroform. The solution is dried and evaporated in vacuo to yield the title compound.

B. 17,21-bis(Acetyloxy)-9-bromo-11β-hydroxy-4,5-secopregn-3-yne-5,20-dione

A solution of 17,21-bis(acetyloxy)-4,5-secopregn-9(11)-ene-3-yne-5,20-dione (25 mmoles) in 45 ml of dioxane is diluted with 9 ml of water and 2.2 ml of a solution of 4.2 ml of 70% perchloric acid diluted to 30 ml with water is added. At the same time, 0.32 g of N-bromoacetamide is added. The solution is stirred in the dark for 30 minutes and 20 ml of 5% sodium sulfite solution is added. The solution is partitioned between chloroform and water and the chloroform solution is dried and evaporated to give the title compound.

EXAMPLE 26

17,21-bis(Acetyloxy)-9-fluoro-4,5-secopregn-3-yne-5,11,20-trione

Following the procedure of Example 1, but substituting 9-fluoro-17,21-dihydroxypregn-4-ene-3,11,20-trione for 9-fluoro-11β,17,21-trihydroxypregn-4-ene-3,20-dione, the title compound is obtained.

What is claimed is:

1. A compound having the structure

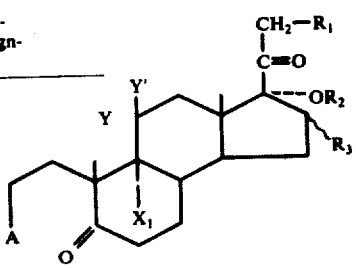

wherein A is —CH=CH$_2$ or —CH$_2$CH$_3$; X$_1$ is hydrogen, chlorine, bromine or fluorine; R$_1$ is hydrogen, hydroxyl,

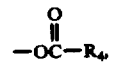

chlorine, bromine, fluorine or iodine; R$_2$ is hydrogen or

R$_3$ is hydrogen, α-methyl, β-methyl, or methylene; R$_4$ is lower alkyl or phenyl; and Y is hydrogen and Y' is hydroxyl or together Y and Y' are =O; wherein lower alkyl is alkyl of 1 to 7 carbon atoms.

2. A compound in accordance with claim 1 wherein A is —CH=CH$_2$.

3. A compound in accordance with claim 1 wherein A is —CH$_2$CH$_3$.

4. The compound in accordance with claim 3 having the name 9-fluoro-11β,17,21-trihydroxy-4,5-secopregnane-5,20-dione.

5. A compound in accordance with claim 1 wherein R$_1$ is hydroxyl.

6. A compound in accordance with claim 1 wherein R$_1$ is

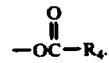

7. A compound in accordance with claim 1 wherein R$_2$ is hydrogen.

8. A compound in accordance with claim 1 wherein R$_2$ is

9. A compound in accordance with claim 1 wherein R₁ is

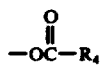

and R₂ is

10. A compound in accordance with claim 1 wherein R₃ is hydrogen.

11. A compound in accordance with claim 1 wherein R₃ is α-methyl.

12. A compound in accordance with claim 1 wherein R₃ is β-methyl.

13. A compound having the structure

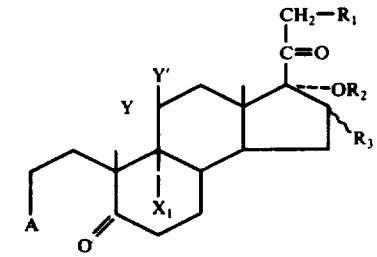

wherein A is —CH=CH₂, —CH₂CH₃, or

X₁ is hydrogen, chlorine, bromine or fluorine; R₁ is chlorine, bromine, fluorine or iodine; R₂ is hydrogen or

R₃ is hydrogen, α-methyl, β-methyl, or methylene; R₄ is lower alkyl or phenyl; and Y is hydrogen and Y' is hydroxyl or together Y and Y' are =O; wherein lower alkyl is alkyl of 1 to 7 carbon atoms.

* * * * *